United States Patent [19]

Hanson et al.

[11] Patent Number: 5,709,874
[45] Date of Patent: Jan. 20, 1998

[54] DEVICE FOR LOCAL DRUG DELIVERY AND METHODS FOR USING THE SAME

[75] Inventors: Stephen R. Hanson, Stone Mountain; Neal A. Scott, Atlanta; Spencer B. King, III, Atlanta; Laurence A. Harker, Atlanta, all of Ga.

[73] Assignee: Emory University, Atlanta, Ga.

[21] Appl. No.: 660,203

[22] Filed: Jun. 3, 1996

Related U.S. Application Data

[63] Continuation of Ser. No. 188,248, Jan. 28, 1994, Pat. No. 5,523,092, which is a continuation-in-part of Ser. No. 46,622, Apr. 14, 1993, Pat. No. 5,399,352.

[51] Int. Cl.$^6$ ................................................. A61M 25/088
[52] U.S. Cl. ........................... 424/423; 604/96; 604/101; 604/264; 604/280; 604/281
[58] Field of Search ........................... 424/423; 604/96, 604/101, 264, 280, 281

[56] References Cited

U.S. PATENT DOCUMENTS

5,256,146  10/1993  Ensminger et al. ................ 604/104

*Primary Examiner*—Carlos Azpuru
*Attorney, Agent, or Firm*—Needle & Rosenberg, PC

[57] ABSTRACT

A device for the local delivery of a substance into a natural tissue conduit in the mammalian body. The device has a substance delivery segment which provides a means for locally delivering a substance into the boundary layer of fluid flowing through the conduit without disrupting the fluid flow therethrough. For example, an indwelling catheter is provided for endovascular delivery of a substance locally to a targeted treatment area. Also provided are methods of locally delivering a substance into a natural tissue conduit in the mammalian body utilizing the device of the present invention.

48 Claims, 5 Drawing Sheets

DEVICE FOR LOCAL DRUG DELIVERY AND METHODS FOR USING THE SAME

CROSS REFERENCE TO RELATED APPLICATION

This application is a continuation of U.S. patent application Ser. No. 08/188,248 filed Jan. 28, 1994, now U.S. Pat. No. 5,523,092 which is a continuation-in-part of U.S. application Ser. No. 08/046,622 Apr. 14, 1993, now U.S. Pat. No. 5,399,352.

This invention was made with government support under Grant Number HL 31469 awarded by the National Institutes of Health. The Government has certain rights in the invention.

FIELD OF THE INVENTION

This invention relates to a device for the local delivery of a substance into a natural tissue conduit to a predetermined site, e.g., a blood vessel, and to methods of therapy utilizing the device. In particular, the invention relates to local delivery of a drug into the boundary layer of fluid flowing through a natural tissue conduit, thereby reducing the amount of drug needed to achieve a therapeutic concentration at a predetermined site, such as, e.g., an angioplasty site.

BACKGROUND OF THE INVENTION

One of the most complex and difficult problems that has plagued the medical profession and pharmaceutical industry for decades is the problem of achieving a therapeutic concentration of a drug locally at a target site within the body without producing unwanted systemic side effects. Parenteral or oral therapy of substances directed at treating disease in a particular internal organ must often be given in mounts dependent upon achieving critical systemic blood levels that can produce devastating side effects at other areas in the body. A prime example of a situation where local therapy is needed with drugs that also produce unwanted systemic side effects is the prevention of complications following the placement of a cardiovascular prosthetic device such as a prosthetic vascular graft, patch, or stent used to repair a damaged vessel.

Graft failure is often associated with the inherent thrombogenicity of the blood contacting surface of the prosthetic device and with the body's own repair mechanisms which can lead to progressive stenotic occlusion due to neointimal fibrosis and hyperplasia. Systemic therapy aimed at preventing coagulation and thrombosis locally at the graft site is often complicated by bleeding at other sites. Likewise, systemic treatment with growth mediators or chemotherapeutic agents can produce a hyperplastic or hypoplastic response in tissue not specifically targeted. Similarly, administration of vasodilators can produce systemic hypotension.

There have been many attempts to render the vascular grafts themselves less thrombogenic, e.g., by coating the luminal surface of the graft with non-thrombogenic polymers (U.S. Pat. No. 4,687,482), cells (U.S. Pat. No. 5,037,378) or with anticoagulant drugs in a polymer coating (PCT Application WO 91/12279). Although these attempts have improved the success associated with graft placement, complications with clotting, thrombosis, and restenosis, especially that seen due to fibroplasia and smooth muscle proliferation, still abound.

Likewise, there have been many attempts to effectuate local drug delivery via endovascular means. Percutaneous transluminal coronary angioplasty (PTCA) balloon dilation catheters have been designed with coatings of drugs on the external surface of the balloon (e.g., U.S. Pat. Nos. 5,102,402 and 5,199,951). Other PTCA catheters contain perforations in the wall of the PTCA balloon for infusion of drugs such as the Wolinsky catheter or the balloon within a balloon design seen in U.S. Pat. No. 5,049,132. These catheters, however, often disrupt blood flow and reduce distal tissue perfusion. Other catheters such as the Stack perfusion catheter and the catheter embodied in U.S. Pat. No. 5,181,971 were designed to facilitate drug delivery without disrupting distal tissue perfusion. These devices, however, are limited in their clinical applications, are bulky, and cannot be anchored in the vessel proximal to the targeted treatment area or utilized in non-vascular applications.

Therefore, there exists a need in the art for a means and a method of providing local therapy which can sustain high local concentrations of therapeutic drugs at a predetermined site, e.g., a site of vessel repair, without producing unwanted systemic side effects. There especially exists a need to provide minimal concentrations of therapeutic agents directly to the boundary layer of blood flow near the vessel wall just proximal to a targeted treatment area which greatly reduces the mount of drug needed to achieve a therapeutic result.

There also exists a need to provide effective local therapy for treatment of cancer and other diseases in many areas of the body such that the chemotherapy can be localized to targeted tissues, thereby preventing unwanted systemic side effects from systemic administration.

SUMMARY OF THE INVENTION

The present invention satisfies the need to provide localized therapy to targeted tissues by providing a means to locally deliver a substance into any natural tissue conduit of the mammalian body and thereby provide localized therapy to targeted tissues. Alternate embodiments of the invention can be utilized to provide local drug delivery to a predetermined site in any conduit, including but not limited to, lymphatic vessels, bile ducts, ureters, the intestinal tract, and the respiratory tree. For example, a transitional cell carcinoma of the bladder can be effectively treated with chemotherapeutic agents by insertion of the device of the present invention into a ureter and administering the appropriate drug. Substances delivered into the boundary layer of fluid flowing through the tissue conduit (near the vessel wall) greatly reduce the amount of the substance needed to achieve a therapeutic result at the target treatment area.

In one embodiment, the drug delivery device is a low profile, indwelling infusion catheter comprised of a specially designed substance delivery segment for delivery of a substance to a predetermined site within a natural tissue conduit in the mammalian body. The substance delivery segment allows for direct delivery of a substance, e.g., a drug, to the boundary layer of fluid flowing through the conduit without disrupting normal fluid flow through the conduit.

Also provided are methods for locally delivering a substance to a predetermined site within a natural tissue conduit. For example, thrombus formation can be prevented at a coronary angioplasty site by delivering small mounts of an anticoagulant directly to the PTCA site utilizing the methods of and devices of the invention.

The present invention also provides a device for local delivery of a drug to a graft site comprised of a vascular graft with a porous portion and a reservoir for the drug attached to the external surface of the graft and overlying the porous portion such that the interior of the reservoir is in fluid communication with the luminal, blood flow contacting surface of the vascular graft via the porous portion wherein a drug placed in the reservoir is delivered to the luminal surface of the graft. The present invention also provides a vascular patch constructed in like fashion. One embodiment of the present invention, provides a tubing attached to and in communication with the reservoir such that the reservoir can be refilled with drug or the drug changed as therapeutic needs change. Another embodiment of the invention further comprises a pump connected to the tubing to deliver drug to the reservoir and to maintain a desired pressure within the reservoir. The present invention also provides methods for treating or preventing, including but not limited to, coagulation, thrombus formation, fibrosis and restenosis associated with vascular prosthetic devices.

DETAILED DESCRIPTION OF THE ILLUSTRATIVE EMBODIMENTS

The present invention may be understood more readily by reference to the following detailed description of specific embodiments and the Examples and Figures included therein.

As used in the claims, "a" can mean one or more.

The present invention provides a device for the local delivery of a substance at a predetermined site in a natural tissue conduit in the mammalian body. The phrase "natural tissue conduit" as used herein means any area of the mammalian body which functions to transport substances and includes, but is not limited to, e.g., blood vessels of the cardiovascular system (arteries and veins), vessels of the lymphatic system, the intestinal tract (esophagus, stomach, the small and large intestines, and colon), the portal-caval system of the liver, the gall bladder and bile duct, the urinary system (ureters, bladder and urethra), the respiratory system (trachea, bronchi, and bronchioles), and ducts and ductules connecting endocrine organs to other areas of the body. The devices of the present invention can be used in any mammal or in any animal in which natural tissue conduits are found.

The devices described herein can also be referred to interchangeably as "catheters" and are designed for intraluminal (e.g., endovascular) use in the natural tissue conduits of the mammalian body described above.

As used herein, the phrase "predetermined site" can mean any site within, or accessible by the natural tissue conduit. The predetermined site can be the site where the substance delivery segment of the device is deployed (positioned) within the conduit and can include diseased as well as healthy sections of the conduit. The predetermined site can be proximal (upstream) of a diseased segment of the natural tissue conduit. In particular, the predetermined site can be a site selected for deployment of the substance delivery segment which allows treatment of a target treatment area or organ distal (downstream) of the deployment site which is accessible for therapy via a fluid flowing through the conduit.

Depending upon the context in which used, the phrase "predetermined site" can also refer to the location within the lumen of the conduit (relative to the cross-sectional diameter thereof) at which a substance is delivered into the lumen of the conduit. For example, the predetermined site can be the boundary layer of a fluid flowing through the conduit. As used herein, the "boundary layer" typically comprises an annular ring at the fluid-conduit interface which occupies only about 5% of the conduit cross-sectional area.

The phrase "target treatment area" is meant to include any area intended to receive a beneficial or therapeutic effect of a substance administered by the devices described herein. For example, the target treatment area can be a stenotic lesion in a blood vessel, a developing thrombus, a PTCA site, a localized tumor or the like.

Referring now to the FIGS. 1-8, the first embodiment of the device 10 comprises an elongated flexible tube 12 of a preselected length and diameter. The length and the diameter of the tube 12 will vary, of course depending upon the size of the conduit and the distance between the point of entry therein and the predetermined site where the device 10 is to be deployed. For example, a typical length for a catheter designed for intracardiac deployment via the femoral artery in a human adult can be between about 80 and 200 cm long with an inside tube diameter of between about 1.0 and 4.5 mm, whereas a catheter designed for use in the proximal urethra of an adult male would be between about 5 and 40 cm long and about 0.1 and 3.0 mm in diameter.

Figure 1:
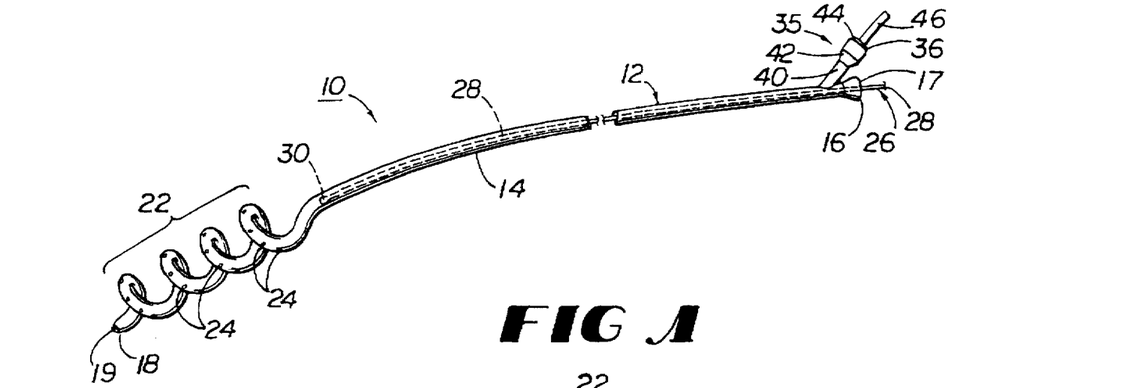
FIG. 1 is a perspective view of the first embodiment of the present invention showing the local drug delivery device as a catheter.
Figure 2:
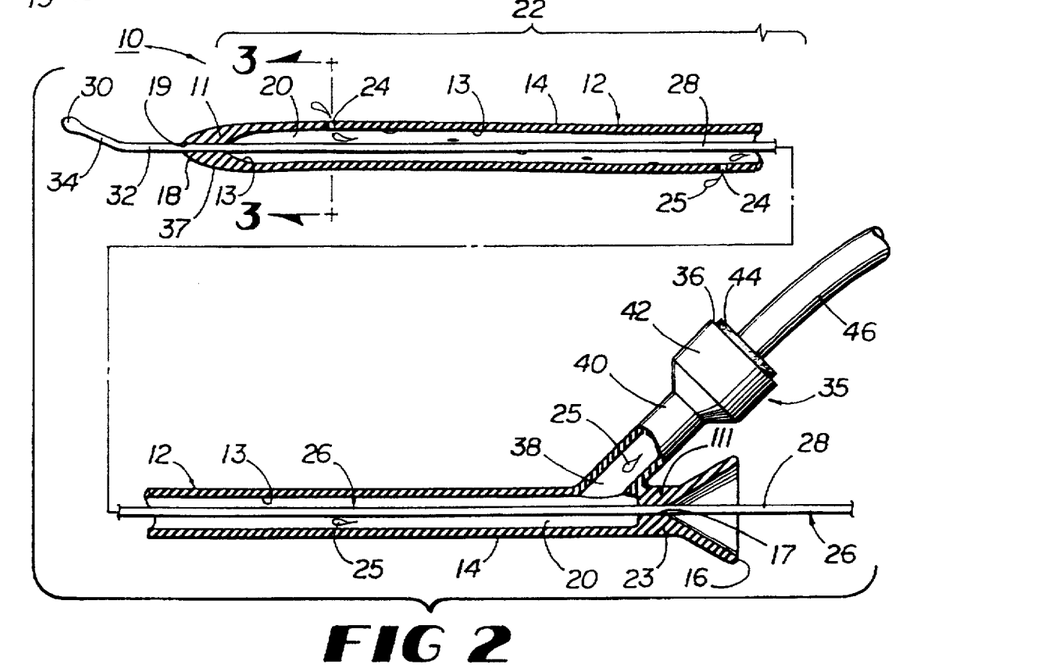
FIG. 2 is a longitudinal cross-sectional view of the first embodiment showing a guidewire inserted in the lumen of the catheter.

In the device 10 shown in FIGS. 1-2, the tube 12 has a body portion 11, an internal surface 13, an external surface 14, a proximal end 16, and an opposite distal end 18. A lumen 20 extends longitudinally through the tube 12 interconnecting the proximal and distal ends 16,18. The proximal end 16 defines an opening 17 and the distal end 18 defines an opening 19 into the lumen 20 of the tube 12. The tube 12 has a substance delivery segment 22 adjacent the distal end 18 which defines a plurality of substance delivery holes 24 through the external surface 14 of the tube 12 which are in fluid communication with the lumen 20 of the tube 12.

A substance, e.g., a fluid 25 containing a drug, can be infused through the substance delivery holes 24 by introducing the substance into the lumen 20 of the tube 12 for delivery into the natural tissue conduit via an introducing means 35 located adjacent the proximal end 16 of the tube 12. The substance introducing means 35 shown in FIGS. 1-2 comprises an infusion port 36 which is in fluid communication with the lumen 20 of the tube 12 adjacent the proximal end 16 thereof. In the embodiment shown in FIG. 2, the luminen 38 of the infusion port 36 is integrally formed with the lumen 20 of the tube 12 in a branched configuration. The external surface 14 of the tube 12 is contiguous with the external surface 40 of the infusion port 36 and the internal surface 13 of the tube 12 is contiguous with the internal surface 39 of the infusion port 36. The lumen 38 of the infusion port 36 opens into a conically shaped female receptacle 42. The female receptacle 42 is designed to removably receive therein a complimentary shaped male plug 44 having a central lumen (not shown) which aligns coaxially with the lumen 38 of the infusion port 36 forming a fluid tight junction. The central lumen of the male plug 44 is in fluid communication with a remote fluid source (not shown) via a tube 46, the lumen (not shown) of which is coaxially aligned with the central lumen of the male plug 44 and lumen 38 of infusion port 36.

As shown in FIG. 2, a fluid 25 containing a desired substance, e.g., a drug, can be introduced into the lumen 20 of the tube 12 by connecting the female receptacle 42 of the infusion port 36 to the complimentary male plug 42 of a remote fluid source and infusing the fluid 25 into the lumen 20 by pumping, injecting, or utilizing gravity flow. Therefore, the substance containing fluid 25 can pass through the introducing means 35, through the lumen 20, through the substance delivery holes 24 to a predetermined site within a natural tissue conduit (not shown).

As the skilled artisan can appreciate, the fluid 25 can be introduced into the device 10 by any of a number of other possible means. Alternatively, for example, the fluid 25 can be introduced directly into the opening 17 defined by the proximal end 16 of the tube 12. Likewise, the infusion port 36 can have any of a number of possible configurations for connection of the remote substance source including, but not limited to, luer lock connectors, snaplock connectors, injection sites, and valved connectors. The substance delivery holes 24 can also be configured in any of a variety of shapes. In the embodiment shown in FIGS. 1-2, the substance delivery holes 24 are round, however, they can also be configured as slit openings through the external surface 14 of the tube 12 which normally remain closed unless fluid 25 is being infused therethrough. The substance delivery holes 24 can also be configured as rectangular openings.

As shown in FIGS. 1-5, the substance delivery segment 22 is moveable among at least three positions but is normally at rest in a first or rest position which has a first shape (as shown in FIG. 1). The first shape of the substance delivery segment 22 comprises a plurality of spiral turns about the longitudinal axis of the device 10 such that the substance delivery segment 22 forms a hollow coil.

In order for the substance delivery segment 22 to easily traverse the lumen 49 of a natural tissue conduit 50 (such as a blood vessel) and reach the predetermined delivery site, the substance delivery segment 22 can be made to assume a second position wherein it has a second shape which is substantially linear (as shown in FIG. 2). A moving means 26 must be applied to the substance delivery segment 22 to cause movement thereof from the first to the second position. By "substantially linear", is meant that the substance delivery segment 22 can assume the linear configuration of the flexible guidewire 28 (or stylette shown in FIG. 14) which is inserted into the luminen 20 of the tube 12. Because the substance delivery segment 22 tends to return to the first position, it exerts a force upon the guidewire 28, such that the uncoiled substance delivery segment 22 takes on a wavy appearance when positioned over the guidewire 28. The guidewire 28 must be flexible yet of sufficient stiffness to maintain the substance delivery segment 22 in the second position.

In the embodiment shown in FIG. 2, the substance delivery segment 22 is maintained in the second position by the moving means 26 which comprises a guidewire 28 having a distal tip 30 which has been inserted into the opening 17 in the proximal end 16 of the tube 12, through the lumen 20, and through the opening 19 of the distal end 18. The guidewire 28 has a first portion 32 which terminates into an upwardly directed second portion 34 which, in turn, terminates into the distal tip 30. The resulting angled attitude of the guidewire tip 30 relative to the longitudinal axis of the tube 12 can be used to direct the device 10 during placement of the substance delivery segment 22 at the predetermined site, e.g., into a branch or bifurcation of an artery or vein.

Figure 4:
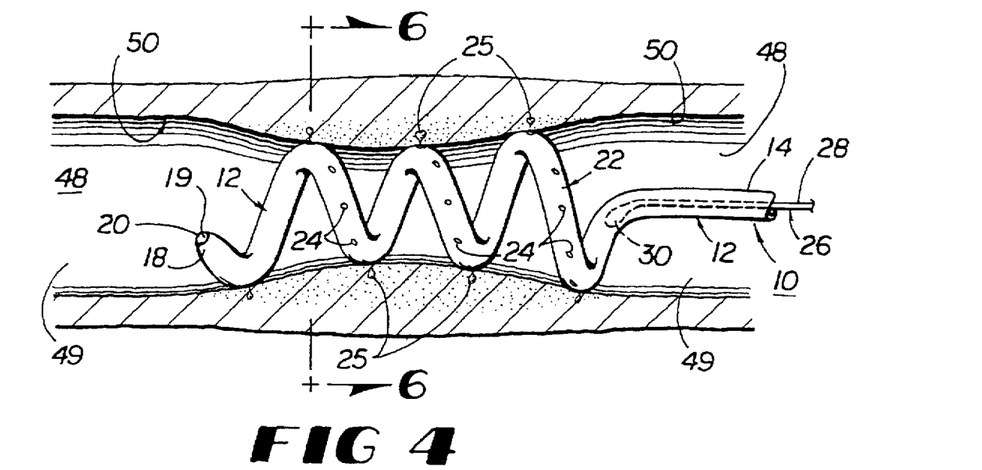
FIG. 4 shows a perspective view of the first embodiment deployed at a stenotic lesion in an artery with the substance delivery segment in the third position.
Figure 5:
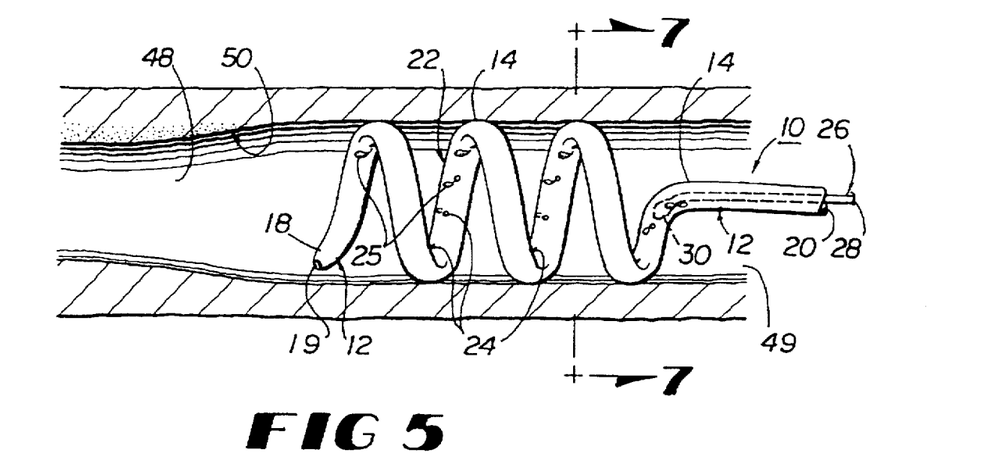
FIG. 5 shows a perspective view of the first embodiment deployed at a predetermined site proximal to a stenotic lesion in an artery with the substance delivery segment in the third position.

Referring now to FIGS. 4-5, the substance delivery segment 22 tends to return to the first, rest (memory) position when the moving means 26 is no longer applied thereto. Upon deployment within a conduit, the substance delivery segment 22 will typically move to a third or operative position which is intermediate the first and second positions as is shown in FIGS. 4-5. The third shape of the substance delivery segment 22 is substantially similar to the hollow coiled configuration of the first shape (shown in FIG. 1). In the third position, the diameter of the hollow coil can be the same or slightly less than the diameter of the hollow coil when the substance delivery segment 21 is in the first position. Moreover, the substance delivery holes 24 are aligned in the virtually the same orientation in the first and third positions. As stated, the substance delivery segment 22 assumes the third position when the moving means 26 is no longer applied thereto, such that the substance delivery segment 22 is capable of exerting a force against the luminal surface 48 of the natural tissue conduit 50, the force being sufficient to anchor the substance delivery segment 22 at the predetermined site within the luminen 49 of the natural tissue conduit 50. The force exerted against the luminal surface 48 is sufficiently great enough to hold the substance delivery segment 22 in a stationary position within the luminen 50 after withdrawal of the guidewire 28, however the force is not so great as to damage the luminal surface 48 of the conduit 50.

Referring to FIG. 2, the proximal end 16 and distal end 18 of the tube 12 define openings 17, 19 into the lumen 10 of the tube 12. In the embodiment shown in FIG. 2, the openings 17, 19 defined by the proximal and distal ends 16, 18 of the tube 12 are moveable between a closed position (not shown) which forms a fluid tight seal of the internal surface 13 at each end 16, 18 and an open position which allows a guidewire 28 to pass through the openings 17, 19. The body portion 11 of the tube 12 forms a thickened annulus 37 at the distal end 18. When the guidewire 28 is partially withdrawn from the substance delivery segment 22 as is shown in FIGS. 4–5, the opening 19 defined by the distal end 18 at the thickened annulus 37 assumes the normally closed position and forms a fluid tight seal of the internal surfaces 13 which overlie the annulus 37 so that a fluid 25 infused through the device 10 will be delivered into the boundary layer of fluid flowing through the lumen 49 of the natural tissue conduit 50 (i.e., the layer of fluid flow adjacent the luminal surface 48 of the conduit 50). The body portion 11 of the tube 12 is also thickened at the proximal end 16 to form a neck 23 which also remains in a normally closed position when the guidewire is not inserted therethrough thereby forming a fluid tight seal of internal surface 13 which overlies the neck 23. Alternatively, the openings 17, 19 defined by the proximal and distal ends 16, 18 can be designed to remain in an open configuration or either one of the openings 17, 19 can move between open and closed positions as described above.

In the embodiment shown in FIG. 2, proximal opening 17 of the tube 12 is funnel or conically shaped to allow for easy insertion of the guidewire 28 into the lumen 20. The body portion 11 of the tube 12 flares into a conical shape proximal to the neck 23 thereby increasing the diameter of the internal surface 13 at the proximal end 16.

Figures 6, 7, 8:
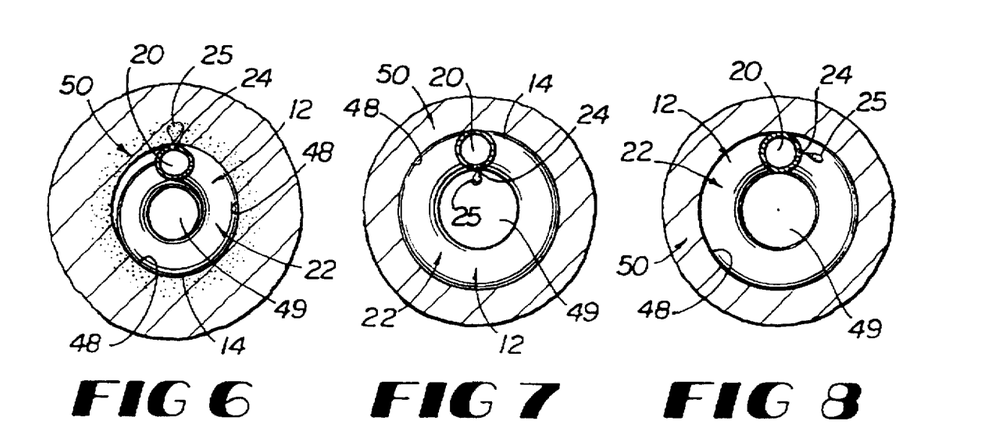
FIG. 6 is a cross-sectional view of the first embodiment taken along lines 6—6 in FIG. 4 showing one possible location of the substance delivery holes.
FIG. 7 is a cross-sectional view of the first embodiment taken along lines 7—7 in FIG. 5 depicting a second possible location of the substance delivery holes.
FIG. 8 is a cross-sectional view of the first embodiment depicting a third possible location of the substance delivery holes.

Referring now to FIGS. 6–8, the substance delivery holes 22 can be positioned on the substance delivery segment 22 at any of a number of preselected locations on the hollow coil formed by the substance delivery segment 22 when it is in the third or deployed position within the lumen 49 of the natural tissue conduit 50. The preselected location can be at any of a number of possible configurations on the substance delivery segment 22. For example, the substance delivery holes 24a (shown in FIG. 6) can be positioned so as to be juxtaposed to the luminal surface 48 of the conduit 50 such that a fluid 25 delivered therethrough directly contacts the luminal surface 48 of the tissue conduit 50 so that the fluid 25 is delivered directly into the wall of the conduit 50. For example, the devices described herein can be utilized to locally deliver drugs directly into the lesion in an artery created by PTCA. Alternatively, the preselected location of the substance delivery holes 24b (shown in FIG. 7) can be such that the holes 24b are adjacent to the luminal surface 48 of the conduit 50 such that a fluid 25 delivered therethrough is delivered into the lumen 49 of the natural tissue conduit 50 adjacent the luminal surface 48 thereof. The preselected location of the substance delivery holes 24c (shown in. FIG. 8) can also be such that the holes are opposite a portion of the external surface 14 of the substance delivery segment 22 which contacts the luminal surface 48 of the conduit 50 so that a fluid 25 delivered therethrough is delivered into the lumen 49 of the natural tissue conduit 50. In each of the configurations described in FIGS. 7–8, the delivery of a fluid 25 through the substance delivery holes 24b–c places the substance into the boundary layer of fluid flow through the natural tissue conduit 50.

FIGS. 9–12 depict a second embodiment of the invention which can also be utilized for the local delivery of a substance to a predetermined site within a natural tissue conduit within the mammalian body. The device 110 is similar to the device shown in FIGS. 1–8 except that it further comprises two separate lumens 120, 121 within the tube 112, a first lumen 120 for the passage of a guidewire 128 therethrough, and a second lumen 121 for substance delivery. In particular, the device 110 comprises an elongated flexible tube 112 of a preselected length and diameter. As previously stated, the preselected length and diameter of the devices described herein can vary depending upon a variety of factors. The tube 112 has an external surface 114, a proximal end 116, an opposite distal end 118, and a first lumen 120 extending longitudinally therethrough interconnecting the proximal and distal ends 116, 118.

Figure 9:
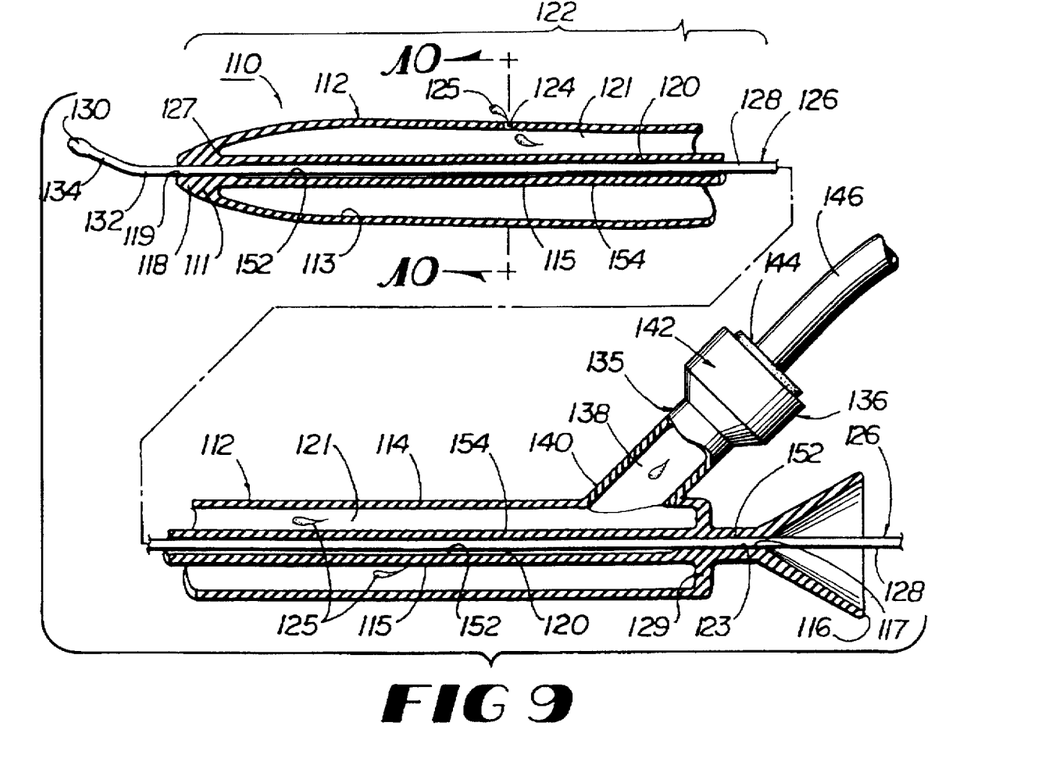
FIG. 9 is a longitudinal cross-sectional view of the second embodiment of the present invention showing the local drug delivery device as a catheter having a guidewire inserted in the first lumen of the catheter.

The tube 112 has a substance delivery segment 122 adjacent the distal end 118 which defines a plurality of substance delivery holes 124 through the external surface 114 of the tube 112. An infusion port 136 is located adjacent the proximal end 116 of the tube 112. A second lumen 121 is located within the body of the tube 112 which interconnects the infusion port 136 with the substance delivery holes 124. A layer of tubing material 115 having first and second surfaces 152, 154 separates the first and second lumens 120, 121 along the longitudinal axis of the tube 112. The second lumen 121 is defined laterally by the internal surface 113 of the tube 112 and medially by the second surface 154 of the tubing material 115.

The second lumen 121 does not extend the entire length of the tube 112, rather it terminates distally at a point 127 where surfaces 113 and 154 meet and proximally at a second point 129 where surfaces 113 and 154 meet. The proximal and distal ends 116, 118 of the tube 112 are integrally formed and contiguous with the body portion 111 of the tube 112 and the internal tubing material 115 thereby forming a fluid tight seal of the proximal and distal ends of the second lumen 121 at points 127 and 129. The second lumen 121, however, is in fluid communication with the substance delivery holes 124 and the infusion port 136 such that a substance, e.g., a fluid 125 containing a drug, can be delivered through the infusion port 136, the second lumen 121, and the substance delivery holes 124 to a predetermined site in a natural tissue conduit (not shown).

Figure 10:
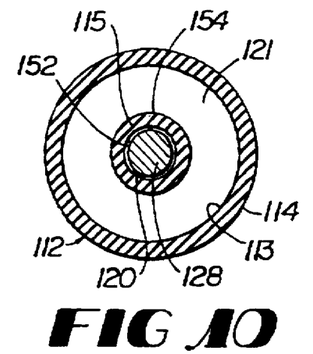
FIG. 10 is a cross-sectional view of the second embodiment taken along lines 10—10 in FIG. 9 showing one possible configuration of the first and second lumens.
Figure 11:
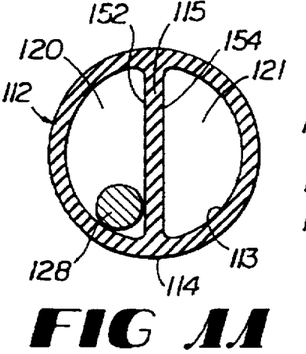
FIG. 11 is a cross-sectional view of the second embodiment depicting a second possible configuration of the first and second lumines.
Figure 12:
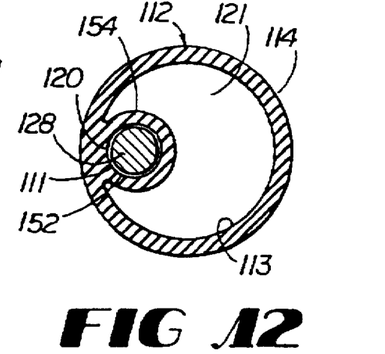
FIG. 12 is a cross-sectional view of the second embodiment taken along approximately the same position as lines 10—10 in FIG. 9 depicting a third possible configuration of the first and second lumens.

FIG. 10 is a cross-sectional view of the embodiment shown in FIG. 9 taken along lines 10—10 in FIG. 9. The tubing material 115 has a first surface 152 which defines the first lumen 120 along the longitudinal axis of the tube 112. The second surface 154 of the tubing material 115 defines the medial luminal surface of the second lumen 121 and the internal surface 113 of the tube 112 defines the lateral luminal surface of the second lumen 121. The guidewire 128 is shown within the first lumen 120 of the tube 112. One can appreciate the many other possible configurations of the of the first lumen 120 relative to the second lumen 121. FIGS. 11–12, for example, show cross-sections of two other possible configurations. In FIG. 11, the internal tubing material 115 bifurcates the tube 112 such that the first and second surfaces 152, 154 of the tubing material 115 form medial surfaces for the first and second lumens 120, 121 respectively. The internal surface 113 of the tube forms the lateral surfaces of the first and second lumens 120, 121. The internal tubing material 115 and the external portion of the tube 112 are integrally formed into a single contiguous unit. The guidewire 128 is shown within the first lumen 120. Alternatively, the first lumen 121 can be eccentrically placed as shown in FIG. 12.

Referring again to FIG. 9, the proximal and distal ends 116, 118 further define openings 117, 119 in the first lumen 120. The body portion 111 of the tube 112 forms a thickened annulus 137 at the distal end 118. The body portion 111 of the tube 112 at the proximal end 116 is also thickened to fore a neck 123. As described for FIG. 2, the openings 117, 119 are moveable between a closed position (not shown) which forms a fluid tight seal of the first surface 152 of the first lumen 120 at each end 116, 118 and an open position which allows a guidewire 128 to pass through the openings 117, 119. When the guidewire 128 is partially withdrawn from the substance delivery segment 122, the opening 119 defined by the distal end 118 forms a fluid tight seal thereof. Alternatively, the openings 117, 119 defined by the proximal and distal ends 116, 118 can be designed to remain in an open configuration or either one of the openings 117, 119 can move between open and closed positions.

In the embodiment shown in FIG. 9, the proximal opening 117 at the proximal end 116 of the tube 112 is funnel or conically shaped to allow for easy insertion of the guidewire 128 into the luminen 120. The body portion 111 of the tube 112 flares into a conical shape proximal to the neck 123, thereby increasing the diameter of the first surface 152 of the first lumen 120 at the proximal end 116.

As was described for the first embodiment, the substance delivery segment 122 is moveable among at least three positions: a first or resting position wherein it has a first shape (similar to the embodiment shown in FIG. 1); a second position wherein it has a second shape (as shown in FIG. 2); and a third or operative position operative position wherein it has a third shape (similar to the embodiment shown in FIGS. 4–5). The third position is intermediate the first and second positions.

In the embodiment shown in FIG. 9, the substance delivery segment 122 moves among the first, second and third positions in the same manner as the substance delivery segment shown in FIGS. 1, 2, 4 and 5 and previously described. However, the substance delivery segment 122 is maintained in the second position by a moving means 126 which comprises a guidewire 128 having a distal tip 130 which has been inserted into the opening 117 at the proximal end 116 of the tube 112, through the first lumen 120, and out of the opening 119 at the distal end 118 thereof. The guidewire 128 has a first portion 132 which terminates into an upwardly directed second portion 134 which, in turn, terminates in the distal tip 130. The resulting angled attitude of the guidewire tip 130 relative to the longitudinal axis of the tube 112 can be used to direct the device 110 during placement of the substance delivery segment 122 at the predetermined site, e.g., into a branch of a bronchus, such as into a bronchiole.

A fluid 125, e.g., containing a substance such as a drug, can be infused through the substance delivery holes 124 by introducing the substance into the lumen 120 of the tube 112 for delivery into the natural tissue conduit via an introducing means 135 located adjacent the proximal end 116 of the tube 112. The substance introducing means 135 shown in FIG. 9 comprises an infusion port 136 which is in fluid communication with the second lumen 121 of the tube 112 adjacent the proximal end 116 thereof. The lumen 138 of the substance introducing means 135 is integrally formed with the second lumen 121 of the tube 112 in a branched configuration. The external surface 114 of the tube 112 is contiguous with the external surface 140 of the infusion port 136. The lumen 138 of the invasion port 136 opens into a conically shaped female receptacle 142. The female receptacle 142 is designed to removably receive therein a complimentary shaped male plug 144 having a central lumen (not shown) which aligns coaxially with the lumen 138 of the infusion port 136 forming a fluid tight junction. The central lumen of the male plug 144 is in fluid communication with a remote fluid source (not shown) via a tube 146, the lumen (not shown) of which is coaxially aligned with the central lumen (not shown) of the male plug 144.

As shown in FIG. 9 (and similarly previously described for the embodiment shown in FIG. 2), a fluid 125 can be introduced into the second lumen 121 of the tube 112 by connecting the female receptacle 142 of the infusion port 136 to the complimentary male plug 142 of a remote fluid source and infusing the fluid 125 into the second lumen 121 by pumping, injecting, or utilizing gravity flow.

Figure 13:
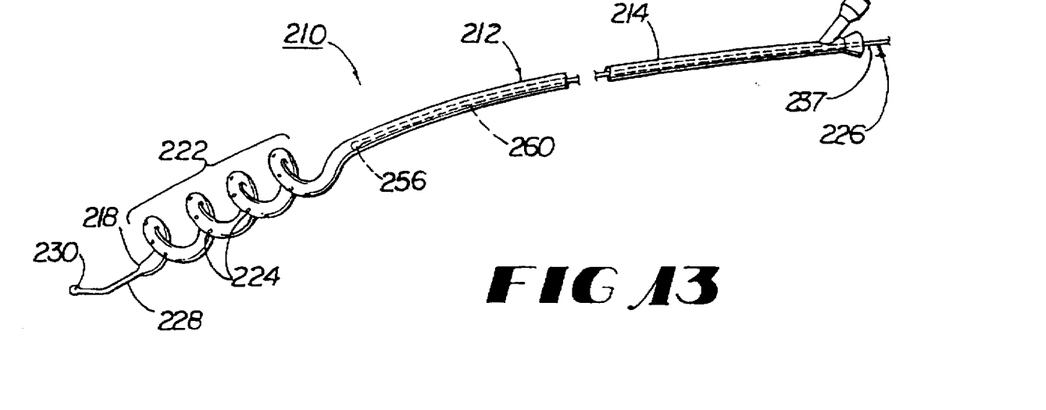
FIG. 13 is a perspective view of the third embodiment of the present invention.
Figure 14:
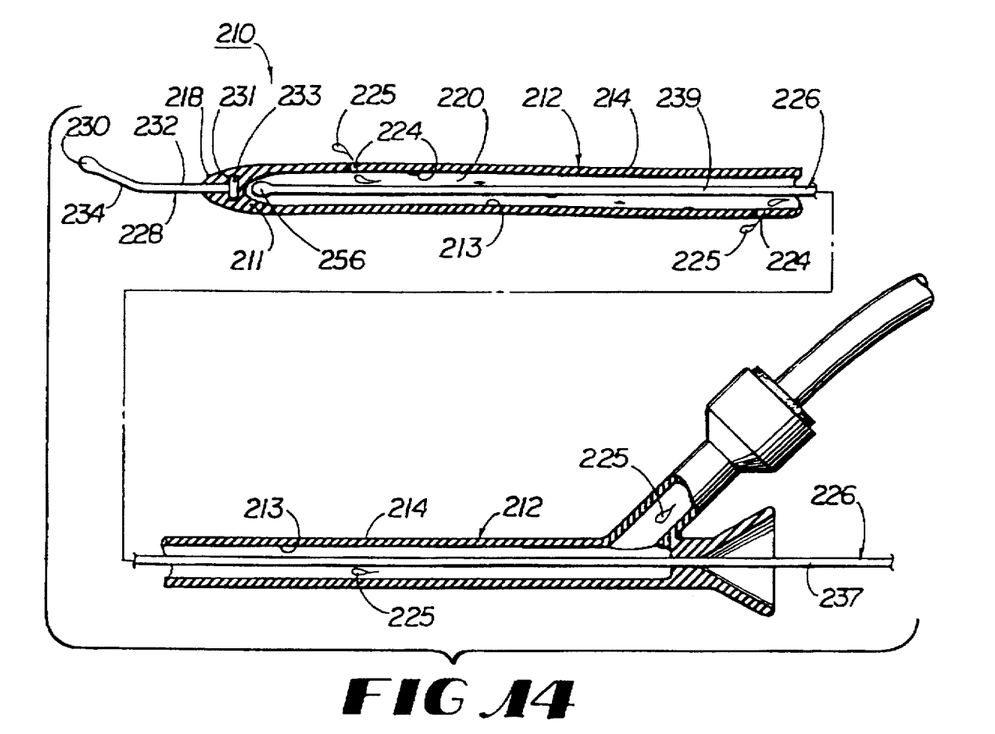
FIG. 14 is a cross-sectional view of the fourth embodiment of the present invention.

Referring now to FIGS. 13–14, the present invention also provides alternative third and fourth embodiments of the drug delivery devices described herein (e.g., the embodiment shown in FIGS. 1–2) wherein the body portion 211 at the distal end 218 of the tube 212 forms a fluid tight seal of the lumen 220 of the tube 212 and the device 210 further comprises a guidewire 228 having a distal tip 230 which is mounted in the body portion 211 of the tube 212 at the distal end 218 thereof. The guidewire 228 can also be mounted on the external surface 214 of the body portion 211 at the distal end 218 of the tube 212. In the embodiment shown, the guidewire 228 has an anchoring portion 233 with shoulders 231 which terminate into the first portion 232. The anchoring portion 233 of the guidewire 228 is cast or molded into the distal end 218 of the body portion 211 of the tube 212. The shape of the anchoring portion 229 can be selected from among many shapes and is not limited to the embodiment shown in FIG. 14. The anchoring portion 233 is integrally formed with the first portion 232 which extends distally from the distal end 218 along the longitudinal axis of the tube 212 and terminates into an upwardly directed portion 234. The upwardly directed portion 234 terminates in the distal tip 230. The total length of the guidewire 228 can vary but is preferably about 4–5 cm. The resulting angled configuration of the guidewire 228 can be used to direct the device 210 during placement of the substance delivery segment 222 within the lumen of the natural tissue conduit (not shown).

The embodiment of the device 210 shown in FIG. 13 also comprises an opening 260 through the external surface 214 of the tube 212 which is in fluid communication with the lumen 220 of the tube 212 such that at least a portion of a fluid 225 delivered into the lumen 220 of the tube 212 can pass into the natural tissue conduit through said opening 260. For example, a catheter (i.e., any of the various embodiments of the devices described herein) designed for delivery of a drug such as an anticoagulant to an angioplasty site in a coronary artery can also include at least one opening 260 proximal to the substance delivery segment 222 for infusion of a small amount of the drug into the bloodstream just proximal to the substance delivery segment 222. This opening 260 can be used to prevent platelet deposition, coagulation and thrombus formation from occurring on the surfaces of the catheter proximal to the substance delivery segment 222. The opening 260 can be located at any point on the tube 212 between the substance delivery segment 222 and the proximal end 216 but is preferably located between about 0.2 and 40 cm proximal to the substance delivery segment 222. Additionally, the device 210 can have more than one openings 260 and the opening(s) 260 can be selected from among a variety of shapes including, but not limited to circular, rectangular, or of a slit configuration similar to the substance delivery holes described herein.

As described for the first embodiment shown in FIGS. 1–8, the substance delivery segment 222 of FIGS. 13–14 can be made to assume the second position and second shape which is substantially linear (as shown in FIG. 2). This allows the device 210 to easily traverse the lumen of a natural tissue conduit and reach the predetermined delivery site. A moving means 226 must be applied to the substance delivery segment 222 to cause movement thereof from the first to the second position. A stylette 239 having a distal tip 256 is inserted into the lumen 220 of the tube 212 and is passed through the substance delivery segment 222 so that the distal tip 256 is adjacent the distal end 218 of the tube 212. The stylette 239 must be flexible to allow the device 210 mounted thereon to maneuver within the lumen of the tissue conduit, yet be of sufficient stiffness to maintain the substance delivery segment 222 in the second position during delivery to the predetermined site. It is also contemplated that the guidewire configuration and stylette of the alternative embodiment described above and shown in FIGS. 13–14 can be utilized in the embodiment shown in FIG. 9 in which the tube 112 comprises two lumens 120, 121.

The devices described herein can be fabricated from any resilient biocompatible material including, but not limited to, materials selected from the group consisting of polymer, synthetic rubber, natural rubber, metal and plastic or combinations thereof by methods known in the art. In general, the devices constructed from polymers or rubber can be molded or cast as a single element and can be cast such that the substance delivery segment (e.g. the substance delivery segment 22 shown in FIG. 1) is pre-formed into the first shape such that the substance delivery segment normally rests in the first (or memory) position.

The polymers contemplated for use in fabrication of the devices of the invention can be either biodegradable or non-biodegradable polymers or combinations thereof. Examples of suitable non-biodegradable polymers include, e.g., polyurethane, polyethylene, polyethylene terephthalate, polytetrafluoroethylene, ethylene vinyl acetate, polyimid, and nylon. Examples of suitable biodegradable polymers include, polylactic acid and polyglycolic acid.

Suitable metals for construction of the devices described herein include, but are not limited to, metals selected from the group consisting of stainless steel, and tantalum, platinum and nitinol. In a presently preferred embodiment, the substance delivery segment 22 (see FIGS. 1–5) is constructed from nitinol (nickel/titanium alloy) such that the nitinol in the substance delivery segment 22 is normally in the first position (i.e., the rest or memory position) as shown in FIG. 1 when the device is at room temperature, e.g., about 23°–25° C. The substance delivery segment 22 can be made to assume the second position (wherein the second shape of the substance delivery segment 22 is substantially linear) by exposing the nitinol to a fluid having a temperature of between about 40°–65° C. but preferably about 55° C.

Exposing the nitinol to a fluid heated to such temperatures causes the metal to expand and straighten so that the substance delivery segment 22 moves from the first position to the second position. The heated fluid therefore can serve as a moving means instead of the guidewires 28 or stylettes 229 previously described. Typically, the substance delivery segment 22 is exposed to the heated fluid by infusing the heated fluid through the lumen 20 of the tube 12 either through the infusion port 36 or through the opening 17 at the proximal end 16 of the tube 12. Suitable fluids which can be utilized to irrigate the nitinol substance delivery segment include, but are not limited to, fluids selected from the group consisting of ringer's solution, lactated ringer's solution, 5% dextrose solution, 10% dextrose solution, normal saline solution, ½ normal saline solution, 5% dextrose and ½ normal saline solution, and sterile water. These fluids also serve as examples of the fluids which can be utilized to carry a substance to the predetermined site by infusion through the devices as described herein. It is contemplated, however, that the guidewire 28 of FIGS. 1–5 and 9 (or the stylette 239 shown in FIGS. 13–14) can be utilized as the moving means 26 and inserted through into the lumen 20 of the nitinol substance delivery segment 22 to assist in placement of the substance delivery segment 20 at the predetermined site within the lumen of the tissue conduit.

Referring again to FIG. 3, an alternative fifth embodiment of the invention provides a semi-permeable membrane 58 covering the external surface 14 of the substance delivery segment 22 and the substance delivery holes 24 defined therein. The semi-permeable membrane 58 can be constructed from any biodegradable or non-biodegradable polymer including the examples of polymers previously discussed herein.

Figure 3:
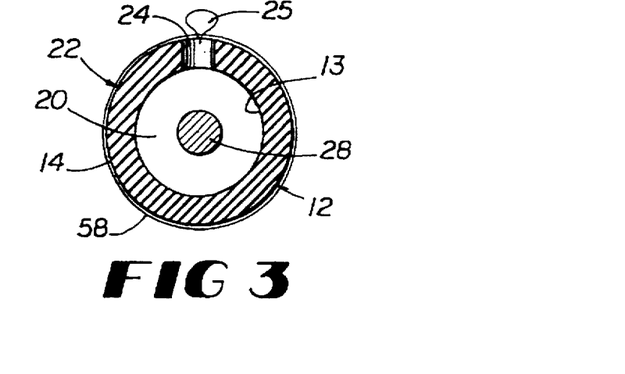
FIG. 3 is a cross-sectional view of the catheter taken along lines 3—3 in FIG. 2.

The delivery of a substance through the substance delivery holes 24 to the predetermined site can occur at a preselected rate through the semi-permeable membrane 58. The preselected rate will very depending upon the permeability of the semi-permeable membrane 58 for the substance of choice and upon the pressure of the infused fluid which is applied to the upstream side of the membrane. The preselected rate can be any flow rate but will typically be between about 0.01 and 1.0 ml/minute.

The devices described herein specifically provide a means for locally delivering a substance to the boundary layer of fluid flowing through a conduit into which they are deployed. For example, the devices described herein can be utilized to provide local drug delivery by utilizing arterial blood flow for prevention or treatment of any disease or condition distal to the site of arterial implantation of the device. Particular examples where the devices of the present invention can be utilized include, but are not limited to, local drug delivery to treat cancer or to maintain perfusion of tissue or organ transplants while the body establishes revascularization of the subject tissue, to prevent restenosis of a PTCA repair or to prevent platelet deposition, coagulation or thrombus formation on a prosthetic device implanted into the cardiovascular system. When the devices described herein are utilized in the cardiovascular system, local delivery of substances is achieved at the predetermined site without disrupting perfusion of tissues distal to the infusion site.

In particular, the present invention provides a method for providing local delivery of a substance to a predetermined site in a natural conduit in the mammalian body, comprising placing a substance delivery device in the lumen of the natural tissue conduit adjacent the predetermined site, the device being in a first position; and delivering the substance to the predetermined site through the substance delivery device wherein the device is in a second position without interrupting the flow of a fluid through the conduit. In a preferred embodiment, the predetermined site is the boundary layer of fluid flowing through the natural tissue conduit and the device is selected from among the devices described herein.

Referring to FIGS. 1–5, one example of a method for providing local delivery of a substance to a predetermined site in a natural conduit in the mammalian body (e.g., an artery) comprises the steps of:

a) introducing the device 10 into the lumen 49 of the natural tissue conduit 50, the device 10 having been premounted on a guidewire 28 having a distal tip 30, wherein the guidewire 28 passes through the lumen 20 of the tube 12 such that the distal tip 30 of the guidewire 28 is adjacent the distal end 18 of the tube 12;

b) advancing the guidewire 28 and premounted device 10 within the lumen 49 of the conduit 50 until the distal tip 30 of the guidewire 28 reaches the predetermined site;

c) removing the guidewire 28 from the lumen 20 of the tube 12 thereby allowing the substance delivery segment 22 to assume the third position at the predetermined delivery site (as shown in FIGS. 4–5);

d) delivering the substance (i.e., a fluid 25 containing the substance) to the predetermined site by infusing the fluid 25 through the substance introducing means 35 (infusion port 36), through the lumen 20 of the tube 12 and through the substance delivery holes 24 such that the fluid 25 containing the substance is delivered to the predetermined site.

Still referring to FIGS. 1–5, an alternative method for providing local delivery of the substances described herein to a predetermined site in a natural conduit in the mammalian body, comprises the steps of:

a) introducing a guidewire 28 having a proximal tip (not shown) and an opposite distal tip 30 into the lumen 49 of the natural tissue conduit 50 and advancing the distal tip 30 to the predetermined site, the proximal tip (not shown) remaining external of the body;

b) inserting the proximal tip (not shown) of the guidewire 28 into the distal opening 17 of the lumen 20 of the device 10 and threading the device 10 over the guidewire 28 until the distal end 18 reaches the distal tip 30 of the guidewire 28, thereby causing the substance delivery segment 22 to be located adjacent the predetermined site;

c) removing the guidewire 28 from the lumen 20 of the tube 12 thereby allowing the substance delivery segment 22 to assume the third position adjacent the predetermined delivery site;

d) delivering the substance (i.e., a fluid 25 containing the substance) to the predetermined site by infusing the fluid 25 through the substance introducing means 35, through the lumen 20 of the tube 12 and through the substance delivery holes 24 such that the fluid 25 containing the substance is delivered to the predetermined site.

In one embodiment of the methods described above, the substance delivery segment 21 of the device 10 is comprised of nitinol and the method further comprises, after the delivering step, the steps of:

a) exposing the nitinol substance delivery segment 22 to a fluid having a temperature of between about 45° C. and 60° C., thereby causing the substance delivery segment 22 to move from the third position to the second position; and b) removing the device 10 from the natural tissue conduit 50.

As contemplated by the present invention, the substance delivered by the devices described herein can be any substance, including any drug, and the device can be used for local delivery of such substances to prevent or treat a variety of disease syndromes or to promote or enhance desired activity within the body. For example, the substance can be an anticoagulant, including but not limited to, heparin, hirudin, hirulog, hirugen, activated and non-activated protein C, synthetic or naturally occurring antagonists of thrombin, and Factor Xa, or other activated or non-activated coagulation protease inhibitors and coagulation factors, e.g., FIX, FVIII, FV, FVIIa and tissue factor.

The devices described herein can also be utilized to deliver a substance which inhibits platelet deposition and thrombus formation or promotes thrombolysis and thrombus dissolution. Examples of such substances include, but are not limited to, plasmin, tissue plasminogen activator (tPA), urokinase (UK), single chain prourokinase (scuPA), streptokinase, prostaglandins, cyclooxygenase inhibitors, phosphodiesterase inhibitors, thromboxane synthetase inhibitors; antagonists of glycoprotein receptors including (GP) Ib,GP IIb/IIIa, antagonists of collagen receptors, and antagonists of platelet thrombin receptors.

Alternatively, the substances delivered by the devices of the present invention can directly affect platelet metabolic function. Examples of such substances include, but are not limited to, prostaglandins, cyclooxygenase inhibitors, phosphodiesterase or thromboxane synthetase inhibitors, inhibitors of calcium transport, or elevators of cyclic adenosine monophosphate (cyclic AMP).

It is also contemplated that the devices of the invention can deliver a substance which prevents restenosis of a blood vessel. Examples of such substances include, but are not limited to, a growth factor, a growth factor inhibitor, growth factor receptor antagonist, transcriptional repressor, translational repressor, antisense DNA, antisense RNA, replication inhibitor, inhibitory antibodies, antibodies directed antagonist, growth factors or their receptors, bifunctional molecules comprising a growth factor and a cytotoxin, and bifunctional molecules comprising an antibody and a cytotoxin.

The substance delivered by the devices of the present invention can also be a vasodilator, such as nitroglycerin, nitroprusside or other nitric oxide liberators. The vasodilator can also include other suitable vasoactive agents such as beta receptor blocking drugs, inhibitors of intra-cellular calcium transport, prostaglandins, thromboxane antagonists, and the like.

The local drug delivery devices of the present invention can be utilized as the device which is placed into the natural tissue conduit in the methods of local drug delivery described above. The methods of local drug delivery of the present invention can be utilized to deliver any substance into any natural tissue conduit in the mammalian body. The methods described herein are meant to include any substance or drug which can be placed in the lumen of the devices described herein. Certain other embodiments of the invention include methods for locally delivering a substance into a natural tissue conduit in the mammalian body wherein the substances are those substances and drugs previously described herein for preventing or treating restenosis, inhibiting platelet deposition and thrombus formation, promoting thrombolysis, or affecting vascular tone. It is also contemplated that the vasodilators and anticoagulants described herein can be used in the methods described above.

Utilizing the methods for predicting downstream concentration of substances (administered by the methods and devices of the present invention) that are taught in the examples, one skilled in the art can determine suitable dosage requirements and treatment regimens for any substance to be delivered to the predetermined site. Dosages and regimens will vary, of course, depending upon the tissue targeted for therapy and upon the particular drug utilized. In particular, the substances for preventing or treating restenosis, inhibiting platelet deposition, and thrombus formation and the vasodilators and anticoagulants described herein can be utilized in the methods for local drug delivery taught herein in amounts determined by the methods taught in the examples and by other optimization procedures known in the art.

One embodiment of the present invention provides a method for locally delivering a substance into a natural tissue conduit wherein the substance inhibits platelet deposition and thrombus formation on a prosthetic cardiovascular device which has been implanted in the cardiovascular system of a subject. The phrase "prosthetic cardiovascular device" includes, but is not limited to, devices such as tubular synthetic grafts, extracorporeal circuits, artificial kidneys, ventricular assist devices, total heart prostheses or oxygenators. As one skilled in the art can appreciate, the method can include, but is not limited to, any of the substances which inhibit platelet deposition and thrombus formation described herein.

The devices and methods of therapy described herein achieve very high drug concentrations locally while minimizing total drug requirements and circulating drug levels, therefore allowing for the efficient use of agents which are available in limited amounts or which could produce side effects. The examples contained herein provide: 1) a theoretical analysis of the convective diffusion problem for the local infusion flow geometry; 2) in vitro studies with measurements of boundary layer drug concentrations distal to infusion sites; and 3) results of studies conducted utilizing a baboon ex vivo shunt system and the local delivery devices of the present invention to block distal thrombus formation.

The examples specifically show that:
1. In typical usage situations drug concentration at the boundary layer of blood near the vessel wall are about 200 times greater than the average drug concentration (averaged over the entire vessel cross section).
2. Local administration of antithrombotic agents reduces total dose requirements (vs. intravenous therapy) by nearly 3 orders of magnitude for agents having short in vivo half lives, e.g., PPACK antithrombin(D-Phe-Pro-Arg chloromethyl ketone).

The following examples document the reproducibility and efficiency of the methods of therapy and the devices described herein.

EXAMPLES

Throughout this application, various publications are referenced. The disclosures of these publications in their entireties are hereby incorporated by reference into this application in order to more fully describe the state of the art to which this invention pertains.

I. Theoretical analysis. The theoretical problem of predicting downstream wall or boundary layer concentrations of material infused through the luminal wall of a 4 mm i.d. tube having 100 ml/min luminal blood flow, typical of medium-sized and coronary arteries has been solved by the present invention. In brief, a supercomputer was used to numerically solve the 2-dimensional Navier-Stokes and species conservation equations using a finite volume element program (Fluent, Inc., Lebanon, N.H.). The analysis predicts that when the drug-containing buffer is infused through the wall of the device described herein at a low rate (0.05–0.1 ml/min), then the wall concentration of drug at 1–5 cm downstream will be 10–20% of the drug concentration in the infusate, i.e., infused materials are diluted 80–90%, but achieve wall concentrations 200 times greater than would be obtained by infusing drug uniformly over the entire tube cross section. Infused material is confined to a very thin boundary layer (approximately 250 microns thick) along the tube wall. Wall drug concentration is therefore determined by the volume and concentration of drug infused. Since at higher infusion rates (>1 ml/min) it is possible to nearly saturate the distal vessel wall with infusate, we chose in subsequent experimental studies to infuse highly concentrated reagents at a low rate (0.05–0.1 ml/min) to avoid significant buffer dilution of blood at the vessel wall.

II. In vitro studies demonstrating boundary layer flow characteristics. In brief, the device utilized in the in vitro studies consisted of a short length (approximately 2 cm) of a standard expanded TEFLON® vascular graft (GORE-TEX®, 30µ internodal distance) having an inner diameter of 4.0 mm. Likewise, for grafts of this type, the preferred range of internodal distance, a measure of porosity, can range from about 10µ to 90µ.

A silicone rubber cuff-reservoir was placed around the graft for infusion of agents through the graft wall, which, therefor, can enter the flow stream only at the portion of the reservoir overlying the graft interface. To study this system in vitro, Evan's blue dye was infused (0.05–0.1 ml/min) with water flow through the device (30 ml/min) scaled for the viscosity difference between water and blood to simulate 100 ml/min blood flow. Dye entered the lumenal space uniformly, around the entire graft circumference. Dye sampling was performed using collection cuffs placed 1–3 cm downstream. Concentration values, obtained by colorimetric analysis, were within 10% of those predicted theoretically (presumably since the experimental flow conditions were not theoretically perfect). Nonetheless, the excellent agreement between theory and experiment confirmed that the theoretical analysis of boundary flow characteristics was accurate.

III. Ex vivo studies with arteriovenous shunts. To document the efficiency of this boundary layer method of local drug delivery, a local drug delivery device as described herein and provided by the present invention was inserted into the lumen of an extension segment of a baboon femoral arteriovenous shunt and the substance delivery segment was placed 2–3 cm proximal to a segment of highly thrombogenic DACRON® vascular graft material. Blood flow through the extension segment was regulated at 100 ml/min, a value typical of those found in the carotid and iliac arteries of approximately 10 kg baboons. The baboon ev vivo shunt model of DACRON® graft thrombosis, and its usefulness for assessing the effects of antithrombotic therapy, has been described previously (See, e.g., S. R. Hanson, et al., *Arteriosclerosis*, 5:595–603, (1985); S. R. Hanson, et al, *J Clin Invest*, 81:149–158, (1988); A. Gruber, et al., *Blood*, 73:639–642, (1989); A. Gruber, et al., *Circulation*, 84:2454–2462, (1991); and W. C. Krupski, et al, *Surgery* 112:433–440, (1992)).

The agent infused was the antithrombin D-Phe-Pro-Arg chloromethyl ketone (PPACK). This agent was chosen since we have previously studied its effects following intravenous infusion in the same thrombosis model, thereby allowing comparison with the local delivery approach. (See, e.g., S. R. Hanson, et al., *Proc Natl Acad Sci USA*, 85:3184–3188, (1988); A. B. Kelly, et al., *Blood*, 77:1006–1012, (1991); and S. R. Hanson, et al., *Thrombosis and Hemostasis*, 65(6):813, (1991)).

Figure 15:
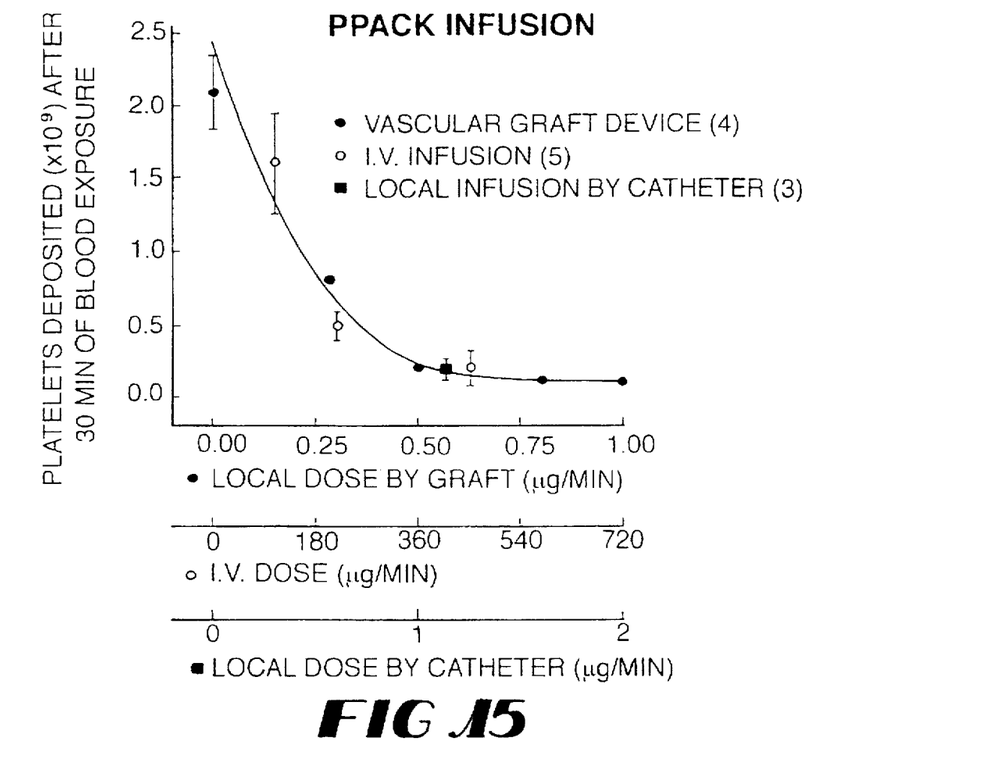
FIG. 15 is a graph showing thrombus inhibition on a DACRON® graft by administration of PPACK in a baboon ex vivo shunt model via conventional systemic intravenous and local infusion routes after 30 minutes of blood exposure.

PPACK was mixed with isotonic saline which was infused at a concentration of 0.1 µg/min. Total platelet deposition was measured over 30 minutes of blood exposure as determined by $^{111}$Indium-platelet imaging. A dose-response curve for local and intravenous (i.v.) administration was virtually coincident for the PPACK infusion. These data imply only that the shape of the i.v. and local infusion dose-response curves for each agent are similar. These data also allow determination of the relative efficiency of i.v. vs. local drug administration. Thus, utilizing the optimization procedures taught herein, the local dose requirement of PPACK for inhibiting platelet thrombus formation was reduced approximately 400-fold (for local infusion vs. systemic i.v. therapy) over 30 minutes of blood exposure (see, FIG. 15). Similarly, laws of first-order clearance kinetics predict that, when agents are infused by the local route, local boundary layer drug concentrations will exceed systemic circulating levels by the same factors (i.e., by 400-fold for PPACK at the 30 minute blood exposure level). This method for predicting dosage requirements can be utilized for other substances to determine an appropriate treatment regimen.

I.V. infusion of PPACK at 45 µg/kg-min into 10 kg baboons having a plasma volume of ~500 ml blocks thrombus formation and produces steady-state plasma levels of >1 µg/ml with an apparent in vivo half life of PPACK of about 2.5 minutes (S. R. Hanson, et al, *Proc Natl Acad Sci USA*, 85:3184–3188, (1988)). The theoretical and in vitro studies (in the optimization procedures discussed herein) predict that in the shunt study, infusion of PPACK solution (5 µg/ml) at a rate of 0.1 ml/min should achieve a wall concentration of 1–2 µg/ml (i.e., 60–80% dilution of infusate), which is essentially that plasma level previously shown to effectively block thrombus formation in the i.v. infusion studies. These data with PPACK therefore denote that the infused material is effectively concentrated in a boundary layer that occupies only approximately 5% of the cross section of a 4 mm i.d. tube having a total flow of 100 ml/min.

In summary, the boundary layer into which effectively all drug is concentrated 2–3 cm downstream comprises an annular ring at the blood-vessel interface occupying only about 5% of the tube cross-sectional area. Thus, total effective drug requirements at that area will be remarkably small. For example, to maintain local PDGF-BB (platelet derived growth factor) levels at 10 ng/ml, we would infuse PDGF solution (100 ng/ml at 0.05 ml/min (i.e., 90% dilution of infusate) or approximately 7 µg per day, a remarkably small requirement for treatment of larger animals.

Therefore, where standard therapeutic levels are known for a substance administered by conventional i.v. (systemic) therapy, the dosage and treatment regimen for local delivery of the substance utilizing the devices of the present invention can be predicted. Further, while the pharmacokinetics of many agents may be complex, these issues are irrelevant for agents having half lives less than several hours, since drug recirculation will contribute very little to the boundary layer drug levels. These data indicate that the methods of the present invention have the advantage of providing local drug levels in known quantities to good approximation to target tissues.

IV. Comparison of substance delivery routes. Three approaches for delivery of PPACK to the surface of a thrombogenic DACRON® graft implanted in an ex vivo baboon artero-venous (a-v) shunt were evaluated for their effectiveness at reducing thrombus formation and platelet deposition after 30 minutes of blood exposure to the graft. Blood flow through the ex vivo a-v shunt was controlled at 100 ml/min for each administration. DACRON® grafts are known to actively thrombose if even a portion of the thrombogenic DACRON® surface is exposed to blood flow (See, A. Gruder, et al., *Blood*, 23:639–642 (1989)). Intravenous systemic administration of PPACK at 400 µg/min was necessary to reduce platelet deposition on the DACRON® graft by 90% at 30 minutes of blood exposure (see, FIG. 15).

Local infusion into the boundary layer of blood flow 2–3 cm proximal to the thrombogenic DACRON® graft was accomplished utilizing the model described in Example II above. A local delivery concentration of 0.5 µg/min at 30 minutes of blood exposure was necessary to reduce platelet deposition on the DACRON® graft by 90% (See, FIG. 15).

Local infusion into the boundary layer of blood flow 2–3 cm proximal to the DACRON® graft was also achieved by placement of a local drug delivery device as described herein within the lumen of the ex vivo shunt. Briefly, an indwelling catheter 10 of the type shown in FIG. 1 having a substance delivery segment 22 was positioned in the lumen of the ex vivo extension segment approximately 2–3 cm proximal to the target delivery site (i.e the DACRON® graft) as is similarly depicted in FIG. 5 which shows the substance delivery segment 22 deployed proximal to an area of arterial stenosis. The coiled configuration of the substance delivery segment 22 and position of the substance delivery holes 24 provided for delivery of infused PPACK directly into the boundary layer of blood flowing through the ex vivo shunt proximal to the DACRON® graft. The PPACK was infused through the infusion port 36, through the lumen 20 of the tube 12, through the substance delivery holes 24, and into the lumen of the ex vivo shunt (not shown). Infusion of PPACK at a rate of 1 µg/min effectively reduced thrombus formation on the DACRON® graft by 90% as compared to controls at 30 minutes of blood exposure. (See, FIG. 15)

Figure 16:
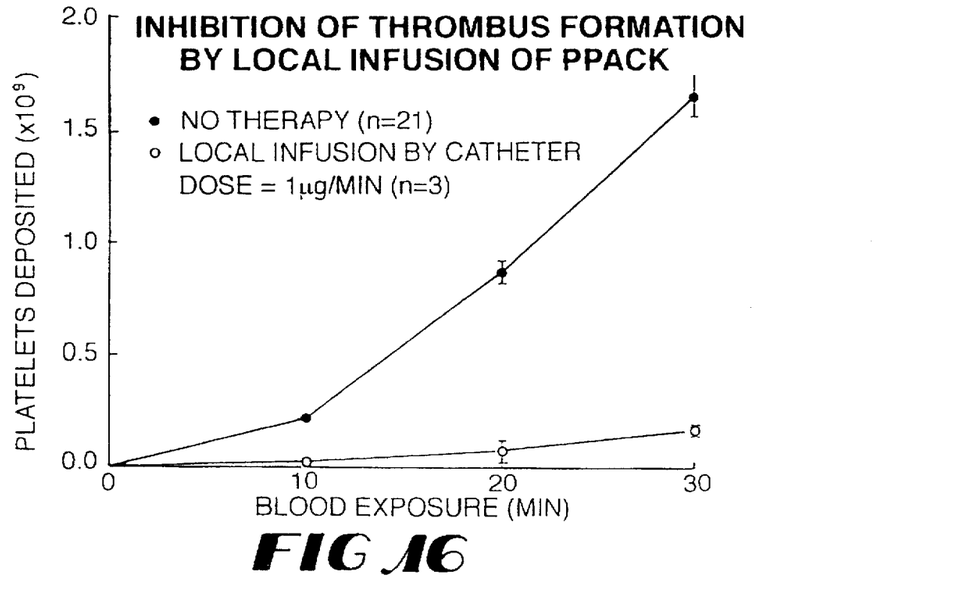
FIG. 16 is a graph showing inhibition of platelet deposition on a DACRON® graft by local infusion of PPACK in a baboon ex vivo shunt model over 30 minutes post blood exposure using the devices described herein.

Platelet deposition on the DACRON® graft surface was measured over 30 minutes in ex vivo shunts in two groups. The graft surface in one group of 3 animals was treated with local delivery of PPACK by infusion utilizing the indwelling catheters described herein at a rate of 1 µg/min. This data was compared to a second group consisting of 21 control animals (see, FIG. 16). Platelet deposition was measured as previously described using $^{111}$Idium-platelet imaging. Platelets accumulated on the surface of the DACRON® graft in a exponential fashion in the control (untreated) animals. Treated animals (PPACK 1 µg/min), however, showed a 90% reduction in (or inhibition of) platelet deposition over 30 minutes.

These data indicate that the indwelling local delivery catheters provided by the present invention show excellent correlation to the boundary flow data as predicted in the theoretical analysis (Example I) and demonstrated in the in vitro local delivery data (Example II). Moreover, the catheter infusion approach reduced the therapeutic drug requirement by a factor of at least 400 times that required by conventional intravenous systemic administration.

Although the present process has been described with reference to specific details of certain embodiments thereof, it is not intended that such details should be regarded as limitations upon the scope of the invention except as and to the extent that they are included in the accompanying claims.

What is claimed is:

1. A device for the local delivery of a substance at a predetermined site in a natural tissue conduit in the mammalian body, the conduit having a luminal surface defining a lumen, comprising:

a) an elongated flexible tube of a preselected length and diameter having an external surface, a proximal end, an opposite distal end, and a lumen extending longitudinally therethrough interconnecting the proximal and distal ends with the proximal end defining an opening therethrough, the tube having a substance delivery segment adjacent the distal end and defining a plurality of substance delivery holes through the external surface which are in fluid communication with the lumen of the tube, the substance delivery segment being moveable among a first rest position wherein it has a first shape, a second position wherein it has a second shape, and a third operative position wherein it has a third shape, the third position being intermediate the first and second positions;

b) means for moving the substance delivery segment from its first position to its second position, the substance delivery segment tending to return to the first position when the moving means is no longer applied to the substance delivery segment; and c) means for introducing the substance into the lumen of the tube for delivery into the natural tissue conduit.

2. A method for providing prolonged localized delivery of a biologically active substance directly into the boundary layer of blood flowing through a predetermined site within a blood vessel without substantially compromising central blood flow through the vessel, the blood vessel having a luminal surface defining a lumen, comprising the steps of:

a) placing a substance delivery device that is adapted to provide prolonged localized delivery of a therapeutic agent directly into the boundary layer of blood flowing through a predetermined site without substantially compromising central blood flow through the vessel in the lumen of the blood vessel adjacent the predetermined site; and b) delivering a substance to the predetermined site via the substance delivery device.

3. The method of claim 2, wherein the substance delivery device is the device of claim 1.

4. The method of claim 2, wherein the substance delivery device is the device of claim 1.

5. The method of claim 2, wherein the substance is a therapeutically effective amount of a drug.

6. The method of claim 2, wherein the predetermined site is an angioplasty site.

7. The method of claim 2, wherein the predetermined site is the boundary layer of blood flowing through the blood vessel upstream of a target treatment area.

8. The method of claim 2, wherein the substance is a therapeutically effective amount of a drug.

9. The method of claim 2, wherein the substance is a therapeutically effective amount of an anticoagulant.

10. The method of claim 9, wherein the anticoagulant is selected from the group consisting of heparin, hirudin, hirulog, hirugen, activated and non-activated protein C, synthetic antagonism of thrombin, Factor VIIa, Factor Xa and activated and non-activated coagulation factors.

11. The method of claim 2, wherein the substance, in a therapeutically effective amount, antagonizes platelet deposition and thrombus formation.

12. The method of claim 11, wherein the substance is selected from the group consisting of: plasmin, tissue plasminogen activator (tPA), urokinase (UK), single chain prourokinase (scuPA), streptokinase; prostaglandins, cyclooxygenase inhibitors, phosphodiesterase inhibitors, thromboxane synthetase inhibitors; antagonists of glycoprotein receptors including (GP) Ib,GP IIb/IIIa, antagonists of collagen receptors, and antagonists of platelet thrombin receptors.

13. The method of claim 2, wherein the substance, in a therapeutically effective amount, affects platelet metabolic function.

14. The method of claim 13, wherein the substance is selected from the group consisting of prostaglandins, cyclooxygenase inhibitors, phosphodiesterase inhibitors, thromboxane inhibitors, inhibitors of calcium transport, and cyclic AMP agonists.

15. The method of claim 2, wherein the substance, in a therapeutically effective amount, prevents restenosis in a blood vessel.

16. The method of claim 15, wherein the substance is selected from the group consisting of a growth factor, a growth factor inhibitor, growth factor receptor antagonist, transcriptional repressor, translational repressor, antisense DNA, antisense RNA, replication inhibitor, inhibitory antibodies, antibodies directed against growth factors, bifunctional molecules comprising a growth factor and a cytotoxin, and bifunctional molecules comprising an antibody and a cytotoxin.

17. The method of claim 2, wherein the substance is a therapeutically effective amount of vasodilator.

18. The method of claim 17, wherein the substance is selected from the group consisting of nitroglycerin, nitroprusside, agents which liberate nitric oxide, and agents which inhibit calcium transport.

19. The device of claim 1, wherein the substance delivery segment assumes the third position when the moving means is no longer applied thereto, such that the substance delivery segment is capable of exerting a force against the luminal surface of the conduit in the third position sufficient to anchor the substance delivery segment at the predetermined site within the lumen of a natural tissue conduit.

20. The device of claim 1, wherein the first shape comprises a plurality of spiral turns of the substance delivery segment about the longitudinal axis of the device such that the substance delivery segment forms a hollow coil having a first predetermined diameter.

21. The device of claim 20, wherein the substance delivery holes are at a preselected location on the coil.

22. The device of claim 1, wherein the third shape comprises a plurality of spiral turns of the substance delivery segment about the longitudinal axis of the device such that the substance delivery segment forms a hollow coil having a second predetermined diameter.

23. The device of claim 22, wherein the substance delivery holes are at a preselected location on the coil.

24. The device of claim 23, wherein the preselected location of the substance delivery holes is that the holes are juxtaposed to the luminal surface of the conduit such that a substance delivered therethrough directly contacts the luminal surface of the tissue conduit.

25. The device of claim 23, wherein the preselected location of the substance delivery holes is that the holes are adjacent to the luminal surface of the conduit such that a substance delivered therethrough is delivered into the natural tissue conduit adjacent the luminal surface thereof.

26. The device of claim 23, wherein the preselected location of the substance delivery holes is that the holes are opposite a portion of the external surface of the substance delivery segment which contacts the luminal surface of the conduit such that a substance delivered therethrough is delivered into the boundary layer of a fluid flowing through the lumen of the natural tissue conduit.

27. The device of claim 1, wherein the distal end of the tube further defines an opening therethrough which is in fluid communication with the lumen of the tube and the opening defined by the proximal end thereof.

28. The device of claim 27, wherein the substance delivery segment is substantially linear in the second position and the moving means comprises a guidewire having a distal tip which is removably insertable into the proximal opening of the lumen of the tube and through the opening of the distal end thereof, the guidewire being sufficiently stiff to maintain the substance delivery segment in the second position, thereby allowing deployment of the substance delivery segment through the conduit to the predetermined site.

29. The device of claim 1, wherein the proximal opening of the lumen of the tube is moveable between a closed position which forms a fluid tight seal and an open position which allows a guidewire to pass therethrough.

30. The device of claim 27, wherein the distal opening of the lumen of the tube is moveable between a closed position which forms a fluid tight seal and an open position which allows a guidewire to pass therethrough.

31. The device of claim 1, wherein the distal end of the tube forms a fluid tight seal of the lumen of the tube and the device further comprises a guidewire having a distal tip and a proximal anchoring end, the guidewire being mounted in the tube at the distal end thereof for guiding the tube through the lumen of the natural tissue conduit to the predetermined site.

32. The device of claim 31, wherein the substance delivery segment is substantially linear in the second position and the moving means comprises a stylette having a distal tip which is removably insertable into the proximal opening of the lumen of the tube, through the lumen of the tube to the distal end thereof, the stylette being sufficiently stiff to maintain the substance delivery segment in the second position, thereby allowing deployment of the substance delivery segment through the conduit to the predetermined site.

33. The device of claim 1, wherein the substance delivery segment is comprised of a resilient biocompatible material selected from the group consisting of polymer, synthetic rubber, natural rubber, metal and plastic preformed to into the first shape such that the substance delivery segment normally rests in the first position.

34. The device of claim 33, wherein the material is a non-biodegradable polymer selected from the group consisting of polyurethane, polyethylene, polyethylene terephthalate, polytetrafluoroethylene, ethylene vinyl acetate, polyimid, and nylon.

35. The device of claim 33, wherein the material is a biodegradable polymer selected from the group consisting of polylactic acid and polyglycolic acid.

36. The device claim 33, wherein the material is a metal selected from the group consisting of stainless steel, and tantalum, platinum and nitinol.

37. The device claim 36, wherein the metal is nitinol and wherein the moving means comprises exposing the nitinol to a fluid having a temperature of between about 40°–65° C.

38. The device of claim 37, wherein the metal is nitinol and wherein the moving means comprises exposing the nitinol to a fluid having a temperature of about 55° C.

39. The device of claim 37, wherein the fluid is selected from the group consisting of ringer's solution, lactated ringer's solution, 5% dextrose solution, 10% dextrose solution, normal saline solution, ½ normal saline solution, 5% dextrose and ½ normal saline solution, and sterile water.

40. The device of claim 1, further comprising a semi-permeable membrane covering the external surface of the substance delivery segment and the substance delivery holes defined therein such that delivery of a substance through the substance delivery holes to the predetermined site occurs at a preselected rate.

41. The device of claim 40, wherein the semi-permeable membrane is comprised of a biocompatible material selected from the group consisting of a biodegradable polymer and a non-biodegradable polymer.

42. The device of claim 41, wherein the semi-permeable membrane is a non-biodegradable polymer selected from the group consisting of polytetrafluoroethylene, ethylene vinyl acetate, polyethylene, and polyethylene terephthalate.

43. The device of claim 40, wherein the substance is a fluid and the preselected rate is between about 0.01 and 1.0 ml/minute.

44. The device of claim 1, wherein the substance introducing means comprises an infusion port attached to the tube adjacent the proximal end which is in fluid communication with the lumen of the tube such that a substance can be delivered through the port and into the lumen of the natural tissue conduit.

45. The device of claim 1, further comprising at least one opening through the external surface of the tube which is in fluid communication with the lumen of the tube, the opening being located between the substance delivery segment and the proximal end of the tube such that at least a portion of a substance delivered into the lumen of the tube can pass into the natural tissue conduit through said opening.

46. The device of claim 1, wherein the conduit is a blood vessel.

47. The device of claim 1, wherein the substance is a drug.

48. A device for the local delivery of a biologically active substance at a predetermined site in a natural tissue conduit in the mammalian body, the conduit having a luminal surface defining a lumen, comprising:

a) an elongated flexible tube of a preselected length and diameter having an external surface, a proximal end, an opposite distal end, and a lumen extending longitudinally therethrough interconnecting the proximal and distal ends with the proximal end defining an opening therethrough, the tube having a substance delivery segment adjacent the distal end and defining a plurality of substance delivery holes through the external surface which are in fluid communication with the lumen of the tube, the substance delivery segment being movable between a resting shape wherein the substance delivery segment comprises a plurality of spiral turns about the longitudinal axis of the device such that the substance delivery segment forms a hollow coil having a first resting diameter and an operative shape wherein the substance delivery segment comprises a plurality of spiral turns about the longitudinal axis of the device such that the substance delivery segment forms a hollow coil having a second operative diameter; and, b) means for introducing the substance into the lumen of the tube for delivery into the natural tissue conduit.

* * * * *